United States Patent
Last-Pollak

(10) Patent No.: US 7,798,812 B2
(45) Date of Patent: Sep. 21, 2010

(54) TEMPORARY DENTAL PROSTHESIS

(75) Inventor: Mordehai Last-Pollak, Nir-Hen (IL)

(73) Assignee: L P M Dental Development Ltd., Moshav Nir-Hen (IL)

( * ) Notice: Subject to any disclaimer, the term of this patent is extended or adjusted under 35 U.S.C. 154(b) by 189 days.

(21) Appl. No.: 11/663,189

(22) PCT Filed: Sep. 15, 2005

(86) PCT No.: PCT/IL2005/000987

§ 371 (c)(1),
(2), (4) Date: Mar. 19, 2007

(87) PCT Pub. No.: WO2006/033098

PCT Pub. Date: Mar. 30, 2006

(65) Prior Publication Data

US 2007/0259315 A1    Nov. 8, 2007

Related U.S. Application Data

(60) Provisional application No. 60/612,250, filed on Sep. 23, 2004.

(51) Int. Cl.
*A61C 8/00* (2006.01)
(52) U.S. Cl. ....................... 433/173; 433/169
(58) Field of Classification Search ............... 433/167, 433/168.1, 169, 179, 171, 172, 173, 174, 433/175, 176, 177
See application file for complete search history.

(56) References Cited

U.S. PATENT DOCUMENTS

| | | | |
|---|---|---|---|
| 3,793,728 A * | 2/1974 | Corbineau | 433/183 |
| 5,213,500 A | 5/1993 | Salazar et al. | |
| 5,674,070 A * | 10/1997 | Fortin et al. | 433/172 |
| 5,766,009 A | 6/1998 | Jeffcoat | |
| 5,885,077 A | 3/1999 | Jeffer | |
| 5,906,489 A | 5/1999 | Khazzam et al. | |
| 6,019,604 A | 2/2000 | Gougeon | |
| 6,136,886 A | 10/2000 | Deguchi | |
| 2005/0042576 A1* | 2/2005 | Oxman et al. | 433/218 |
| 2006/0014120 A1* | 1/2006 | Sapian | 433/173 |
| 2006/0188844 A1 | 8/2006 | Dadi | |

FOREIGN PATENT DOCUMENTS

WO    95/35071 A1    12/1995
WO    2005/018479 A1    3/2005

* cited by examiner

*Primary Examiner*—Cris L Rodriguez
*Assistant Examiner*—Eric Rosen
(74) *Attorney, Agent, or Firm*—The Nath Law Group; Derek Richmond; Robert T. Burns

(57) ABSTRACT

A temporary prosthesis for use during the osseointegration process of an installed dental implant includes load-absorbing properties and is mountable to the implant, providing an aesthetic appearance to the implant site, while preventing or minimizing loads on the implant itself.

24 Claims, 9 Drawing Sheets

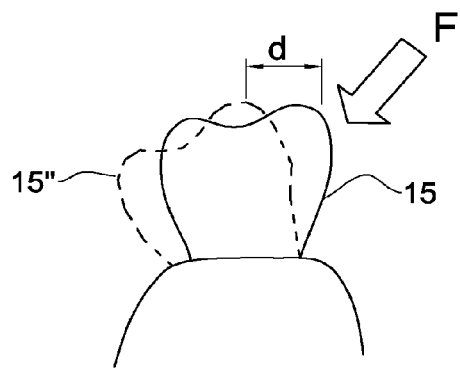
FIG. 2
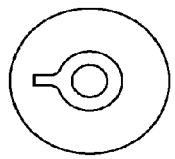
FIG. 3 (a)
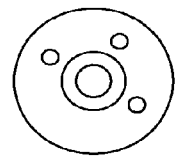
FIG. 3 (b)
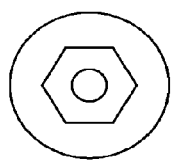
FIG. 4 (a)
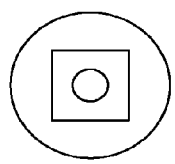
FIG. 4 (b)
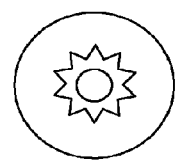
FIG. 4(c)
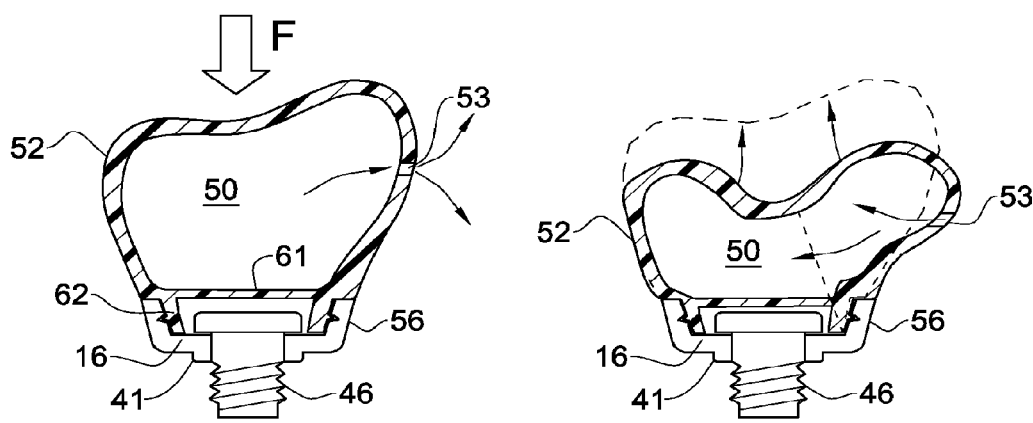
FIG. 5 (a)
FIG. 5 (b)

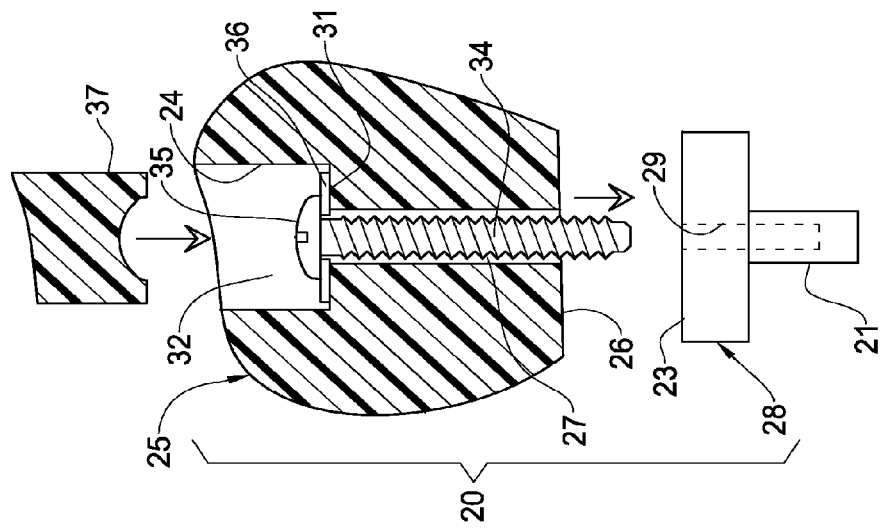
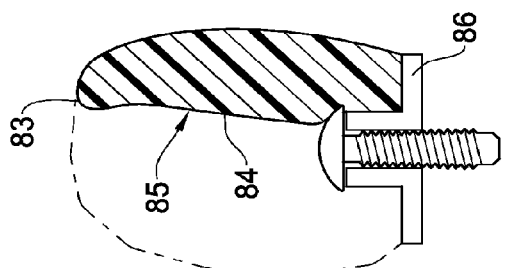
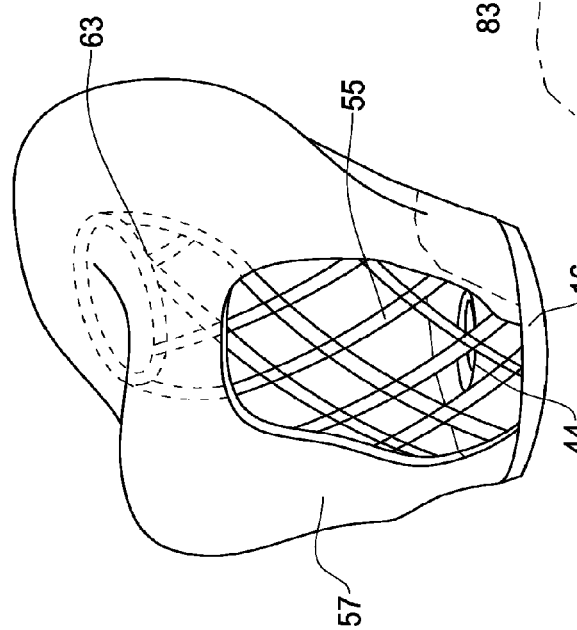
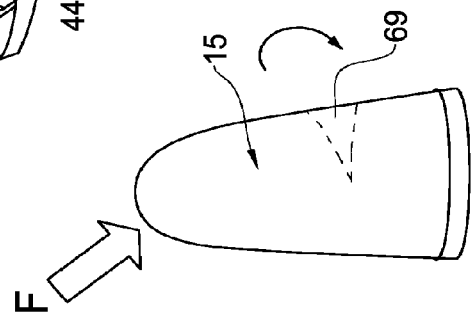

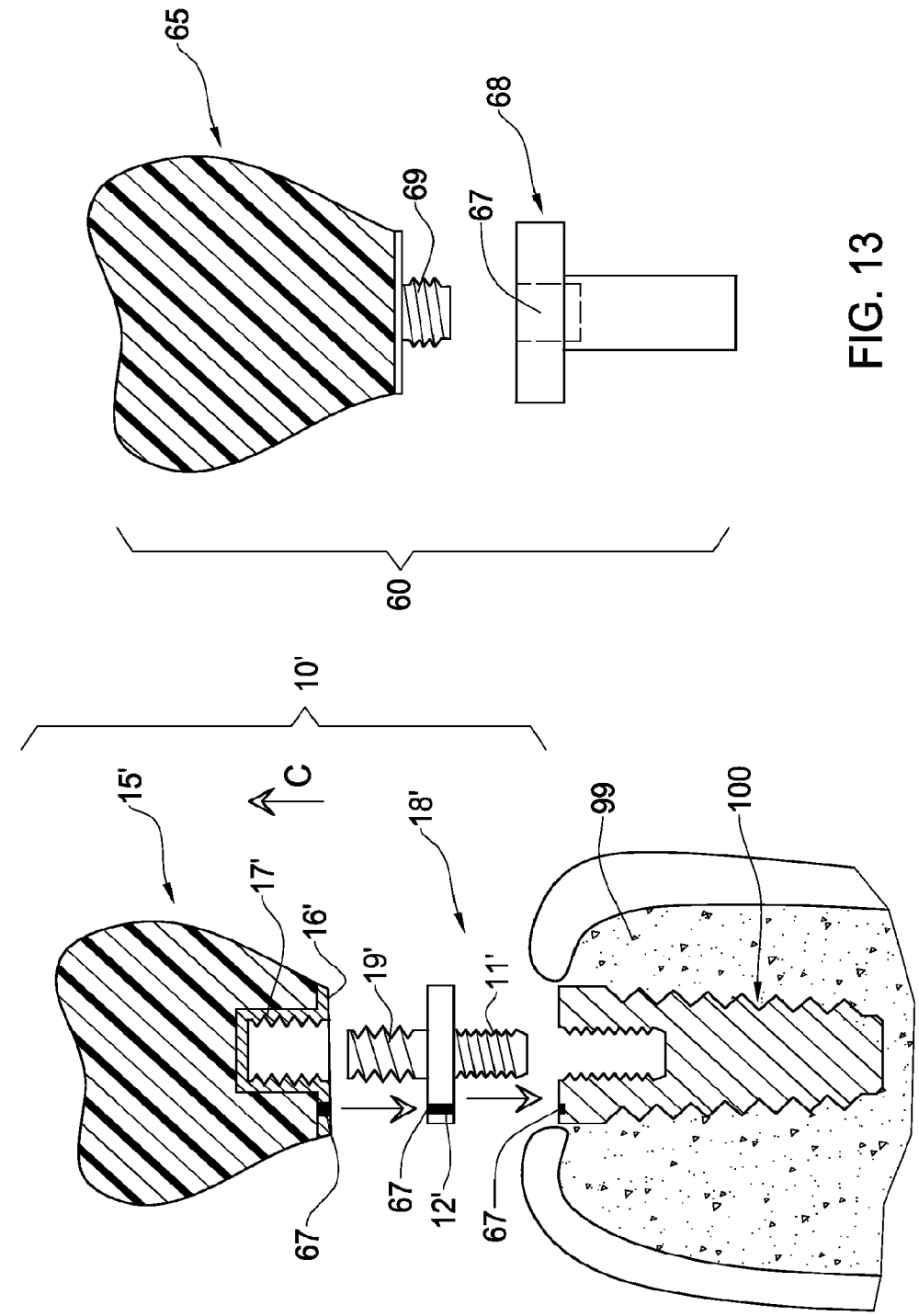

TEMPORARY DENTAL PROSTHESIS

CROSS-REFERENCE

This is a National Phase Application filed under 35 U.S.C. 371 of International Application No. PCT/IL2005/000987, filed Sep. 15, 2005, claiming the benefit under 35 U.S.C. 119(e) of U.S. Provisional Application No. 60/612,250, filed Sep. 23, 2004, the entire contents of each of which is hereby incorporated herein by reference in its entirety.

FIELD OF THE INVENTION

This invention relates to dentistry, in particular to the field of prosthodontics.

BACKGROUND OF THE INVENTION

Dental restoration processes, including replacing the missing tooth or teeth with permanent prostheses mounted on implants embedded in bony tissues of the upper and/or lower jaws, are well known. Fixed prostheses are fixed to the implant in a nominally permanent manner, and are not designed to be removed in the normal use thereof. These are to be contrasted with mobile or implant-supported prostheses, which are removable during normal use thereof and may or may not have an implant structure in the mouth. Both fixed and mobile permanent prostheses provide the appearance of teeth, and mimic the function thereof, allowing food to be masticated etc.

A number of different general procedures are known for implanting such fixed prostheses, and all start with embedding at least one implant, typically made from titanium or other medically compatible metal, in the bony tissues. Typically, one implant is required for each crown prosthesis, and at least two implants for bridge prostheses. In some cases requiring bridge prostheses, though, it may be possible to implant a prosthesis that is anchored at one retainer onto an implant, while at another retainer via a preparation, where there is sufficient healthy tooth left for this purpose.

One such general procedure, the conventional loading procedure, includes a surgical stage and a reconstruction stage. In the surgical stage, a suitable implant is first screwed or tapped into a surgically prepared site in the upper or lower jaw. Then, the gum tissue is closed over the implant, and the patent wears a denture during 3 to 6 months until the osseointegration process is completed, and the implant is firmly anchored in the jaw. During the healing period, the patient usually wears a denture over the closed gum. The denture includes a hard prosthesis that temporarily replaces the structure and function of the missing tooth or teeth, though it may include a softer portion that is adapted for fitting snugly over the gum. In the reconstruction stage part of the implant is exposed by removing a small amount of gum tissue, and a healing cup is mounted onto the implant, not in occlusion with the opposing dentition, and remains in place for a number of weeks until the gums have healed. The healing cup is not a prosthesis, but rather has a standard shape or form having a healing ring on a perimeter thereof that promotes healing of the gum tissue so that the prosthesis can eventually be mounted. The healing cup does not have the appearance of a dental structure, nor does it function as such—in fact this is considered highly undesirable. After this second healing period, the cup is removed, and the crown prosthesis is mounted to the implant, typically via a connecting structure.

This procedure has the advantage of substantially preventing any loading directly onto the implant until this has been firmly anchored onto the bone via osseointegration. The dentures themselves do not directly load the implant, but rather transmit loads to the jaws in a substantially diffused manner. However, the healing cup itself is unsightly and may have an undesirable psychological effect of self-consciousness on many patients. The procedure for a bridge prosthesis is similar to that described above, but carried out on one or both anchoring sites, according to the number of implants that are required.

In a variation of the conventional loading procedure, the permanent prosthesis is attached in a second surgical procedure that takes place some time later than the 3 to 6 month healing period.

A second general procedure, known as the one step procedure (also as "immediate restoration"), is similar to the conventional loading procedure described above, but is a shorter procedure in which the step of closing the gums at the beginning of the osseointegration period is omitted. Accordingly, rather than surgically closing the gum over the implant, a suitable healing cup is instead mounted on the implant immediately, the cup not being in occlusion with the opposing dentition. Thus, healing of the gum tissue is concurrent with osseointegration of the implant. However, this type of procedure, though shorter than the conventional loading procedure and reducing the number of surgical interventions with respect thereto, carries potential risks of infection and of micromovement of the implant due to loads that may be applied to the healing cup when masticating, for example. Further, the esthetically unappealing cup is visible for a considerable period.

A third general procedure, known as immediate loading, is similar to the one step procedure, but is actually even shorter, wherein rather than providing a healing cup for the healing and osseointegration stage, a first prosthesis is mounted to the implant within 2 days after the implant is embedded in the jaw, in occlusion with the opposing dentition, and is used for mastication and so on. In some cases, this prosthesis may be mounted to the implant via a temporary connecting structure that promotes healing of the gum, and this connecting structure may be replaced at a later stage with a permanent connector, together with a second, permanent prosthesis. While a shorter process than the one-step procedure, and while not involving the use of an unsightly healing cup, there is nevertheless a risk of infection, as well as of substantial micromovement of the implant, as the first prosthesis is directly loaded by the regular forces in the intraoral cavity, such as mastication for example, before the implant has been fully anchored in place.

In a variation of the immediate loading procedure, known as the early loading procedure, the first prosthesis is installed after 2 days from installation of the implant, but before 3 months have elapsed.

Another type of procedure is disclosed in U.S. Pat. No. 5,906,489. An implant is disclosed therein for supporting a hard prosthesis that is used for chewing, and includes a base sheet that has a longitudinal axis and a lateral axis. At least two holes extend through the base sheet. A post is connected to the base sheet. The temporary dental implant is installed over a patient's jaw bone by exposing the jaw bone by displacing covering tissue. The base sheet is shaped into a U-shape so that the legs of the U-shape are directed away from the post. The shaped base sheet is installed over the jaw bone by securing the covering tissue to the jaw bone and loading the prosthesis onto the post. The prosthesis is loaded a few days after the temporary implant has been installed, after which the prosthesis is used for chewing.

SUMMARY OF THE INVENTION

The present invention relates to a provisional or temporary substantially non-load bearing fixed dental prosthesis, comprising a prosthesis body and at least one interface adapted for mounting said prosthesis to at least one implant, wherein said prosthesis body is configured for substantially absorbing externally-applied loads acting on the prosthesis body and for minimizing transmission of such external loads to at least a said implant onto which said temporary prosthesis may be mounted.

The prosthesis body may be made from a load-absorbing material, and optionally the load-absorbing material comprises a resilient material capable of absorbing said loads by substantially deforming from a nominal datum shape. Typically, the load-absorbing material deforms elastically when said load is applied thereto, though in other embodiments of the invention, the deformation may be plastic or non-reversible. The deformations are such that very little, if any, of the loads acting on the prosthesis are actually transmitted to the interface and thus to the implant itself. Accordingly, the prosthesis body may undergo linear and/or rotational deformations which may be a significant percentage of its linear dimensions. For example, such linear deformations in any direction within the intraoral cavity, depending on the direction of the applied force may be higher than 1%, typically ranging from up to about 5% to about 50%, and in some cases even above 50%.

Further optionally, the prosthesis body comprises at least one pre-formed weakened structure, such as a cavity, tear, perforations and so on, for example, configured to enable a first part of said prosthesis to deflect about said weakened structure in response to application thereon of a said externally-applied load. Thus, the deflection may be in a rotational sense rather than a linear sense, and again may result in angular deformations of anything from about 1° to about 90°, or even greater than 90°. In some embodiments, the pre-weakened structure is configured to enable said first part of said prosthesis to break off from said prosthesis body in response to application thereon of a said externally-applied load having a magnitude greater than a predetermined threshold, wherein said threshold is correlated to a predetermined safety limit configured to prevent excessive loads being transmitted to a said implant onto which the prosthesis body may be mounted. Such excessive loads may be defined, for example, as the loads which may cause significant micro-movement of the implant.

Examples of suitable load absorbing material may include, but are not limited to, any one or combination of rubber, silicone, nylon, polyethylene, copolymers, plastic, Teflon, compomers, elastomers or other biocompatible materials.

The prosthesis body may be formed substantially as a solid body made of said resilient material. Alternatively, the prosthesis body may be hollow, comprising a cavity and a skin enclosing said cavity made of said resilient material. Alternatively, the prosthesis body may be made of a sponge-like material, comprising a network of interconnected cavities, or of a composite material, made from different types of base materials. Optionally, the prosthesis body may be made from a plurality of layers of suitable materials. Optionally, the prosthesis body is formed as a molded component.

Typically, prosthesis body may deformed under said loads such that at least one part of the external surface of the prosthesis body is displaced and/or rotated from an unstressed datum position by a displacement, wherein under said loads, corresponding to regular masticating actions between the jaws, said displacement may in the range of about 0.5 mm to about 5 mm, by way of example.

Alternatively, the prosthesis body may comprise a load-absorbing structure capable of absorbing said loads by substantially deforming from a nominal datum shape, in a similar manner to that of the load-absorbing material, mutatis mutandis. For example, the prosthesis body may comprise a mesh structure comprising polymeric, or metallic strands, in particular metallic strands made from memory alloy that is configured for providing said datum shape to the prosthesis body, and for reversibly deforming under application of said externally-applied load such that when the load is removed, the prosthesis body assumes said datum shape.

The interface comprises engagement means for engaging the prosthesis—that is connected thereto, reversibly or permanently—with respect to a said implant. Alternatively, suitable engagement means are provided for engaging the prosthesis to the implant, for example a bolt that engages the implant via the prosthesis body and interface. Typically, the interface comprises a surface on said prosthesis body adapted for mounting onto a said implant, and optionally further comprises means for aligning the interface with the implant. The alignment means may comprise a suitable alignment key in one component configured for engagement with a complementary molding on the other component. Alternatively, the alignment means may comprise markings or indicia in the elements which when lined up indicate that proper alignment has been achieved.

Preferably, the interface comprises a healing band at a periphery thereof adapted for promoting healing of gum tissues when said interface is connected to a said implant.

Typically, the interface comprises at least one suitable material including titanium, gold, metal alloys, ivory, porcelain, ceramics, plastics, Teflon, or any other biologically compatible material.

The prosthesis body typically corresponds to a crown, or at least a part thereof, or to a bridge, in which case it comprises at least two spaced interfaces one each adapted for mounting onto separate implants. In the latter case, the prosthesis typically comprises a pontic section connected laterally on either side thereof to one or the other of two retainer portions, wherein each said retainer comprises one or the other of said spaced interfaces.

In one embodiment, the prosthesis body is integrally joined to said interface. In another embodiment, the prosthesis body is reversibly mountable with respect to said interface and is alignable therewith. In the latter case, suitable mounting means are provided for mounting said prosthesis body to said interface.

The present invention also relates to a kit of temporary prostheses, comprising a plurality of different prosthesis bodies and a plurality of interfaces reversibly mountable with respect thereto, wherein each said interface is adapted for mounting to one of a variety of said implants, and where each said interface is adapted for mounting to any one of said plurality of prosthesis bodies.

The present invention also relates to a method for implanting a permanent prosthesis onto at least one implant embedded in an intraoral cavity, comprising:

embedding the or each said implant such that an upper part thereof is exposed with respect to surrounding gingiva;
  during a healing period of the or each implant with respect to bone tissue associated with said embedding in step (a), mounting a temporary prosthesis on the or each said implant, wherein said temporary prosthesis is configured for substantially absorbing externally-applied loads acting thereon and for minimizing transmission of such external loads to the or each said implant; and after said healing period replacing said temporary prosthesis with a permanent prosthesis capable of reacting to and transmitting loads to the or each said implant.

The present invention is also directed at molds for manufacturing said prosthesis body when this is formed as a molded component.

Thus, according to the invention, the provisional or temporary fixed prosthesis covers the implant zone so that the gum tissue is not closed over the implant, and thus no additional surgery is required to then reopen the gum. At the same time, the temporary prosthesis of the invention provides the appearance of a real tooth, while absorbing loads that are normally induced on dental structures in the oral cavity, rather than transmitting the loads to the implant, allowing the osseointegration process to continue substantially without introducing micro-movements.

Herein, reference to load absorbing materials is taken to include energy-absorbing materials, and also to structures which have load absorbing or energy absorbing characteristics, even though they may comprise materials which are not themselves energy absorbing or load absorbing, in each case the absorption of the loads or impact energies being by means of substantial and significant deflection and/or deformation of the material or structure.

BRIEF DESCRIPTION OF THE DRAWINGS

In order to understand the invention and to see how it may be carried out in practice, a number of embodiments will now be described, by way of non-limiting example only, with reference to the accompanying drawings, in which:

FIG. 2 schematically illustrates load-absorbing properties of the embodiment of FIG. 1.

FIGS. 3(a), 3(b) illustrate alternative configurations of an alignment key as seen along X-X in FIG. 1

FIGS. 4(a) to 4(c) illustrate alternative configurations of another alignment key as seen along Y-Y in FIG. 1

FIGS. 5(a) and 5(b) illustrate a variation of the prosthesis body of the embodiment of FIG. 1, when just being loaded and when just being unloaded, respectively.

FIG. 6 illustrates another variation of the prosthesis body of the embodiment of FIG. 1.

FIG. 7 illustrates another variation of the prosthesis body of the embodiment of FIG. 1.

FIG. 8 illustrates another variation of the prosthesis body of the embodiment of FIG. 1.

FIG. 9 illustrates another variation of the embodiment of FIG. 1.

FIG. 12 illustrates another variation of the embodiment of FIG. 1.

FIG. 13 illustrates a variation of the embodiment of FIG. 12.

DETAILED DESCRIPTION OF EXEMPLARY EMBODIMENTS

Figure 1:
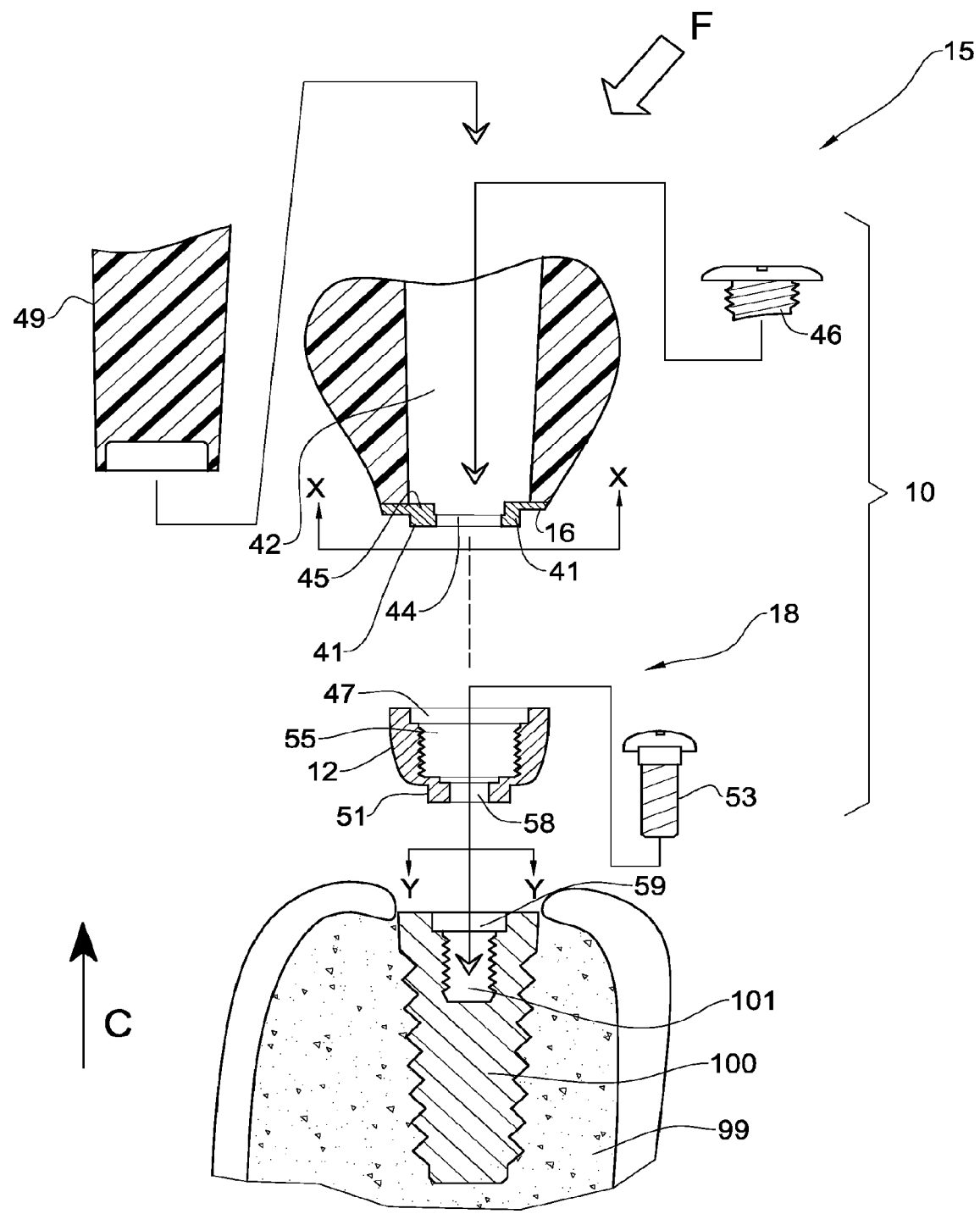
FIG. 1 illustrates in side cross-sectional view a first embodiment of the invention.

A temporary prosthesis according to a first embodiment of the present invention, illustrated in FIG. 1 and generally designated with the numeral 10, comprises a prosthesis body 15, and an interface structure 18 for connection to the dental implant 100 that, in typical use, is already surgically implanted in the bony tissues 99 of the patient. The prosthesis body 15 is capable of absorbing loads by deforming and/or deflecting, and in this embodiment is made from a resilient, non-rigid, flexible material, preferably having an external shape, size, color and shading such that it resembles the tooth that the permanent prosthesis is to eventually replace. Suitable examples of such materials may include rubber, silicone, nylon, polyethylene, copolymers, compomers, elastomers, plastic, Teflon, and other biocompatible materials. The prosthesis body 15 may comprise a single homogenous material, or alternatively comprise different materials suitably missed or arranged therein, comprising for example different densities, elasticity, hardnesses, and so on, for example in layers. At the same time the material used for the prosthesis are biocompatible with the intraoral cavity, and are strong enough such as to survive substantially intact in the oral cavity for a duration of at least 6 months. Alternatively, it is possible to make the prosthesis body from other materials that are not so long lasting, and replace the prosthesis as often as required.

For example, the prosthesis may be a crown prosthesis, as illustrated in FIG. 1, and the shape of the prosthesis body 15 may be such as to be a representation or an exact copy of the healthy shape of the damaged tooth that is being replaced. This tooth may be an adult's or child's incisor, canine, premolar or molar, from the upper or lower jaw, according to the particular case being considered. For this purpose, the body 15 may be made to follow the design of the permanent prosthesis, or may be molded from an impression made from the original tooth, suitably modified if necessary to smooth over cracks and cavities therein, for example. Alternatively, a suitable approximation or match to the missing tooth may be found by choosing a prosthesis body 15 out of set comprising a number of standard prosthesis shapes and sizes that may be provided for this purpose. For example, such a set may comprise a few different standard shapes for canines, molars and incisors, and for each standard shape, a number of different sizes are provided to cater for the dimensional differences between different patients.

The body 15 is thus adapted such as absorbs loads F applied thereto, for example by virtue of intraoral forces induced by mastication and so on, by substantially deforming and/or deflecting in shape to a new shape 15' (FIG. 2). The deformation of the prosthesis body 15 may be localised, such as a dent or the like, or global, where the shape of the whole prosthesis is altered. Such deformations are typically reversible and preferably elastic, enabling the datum original shape to be recovered once the load is removed, and thus enabling the original appearance of the prosthesis body to be restored. By way of example, such deformations may include a displacement d of at least the outer surface of prosthesis body 15 in the order of 0.5 mm to about 5 mm on application of loads F that are normally induced on teeth during mastication, for example.

The prosthesis body 15 further comprises a base 16 that is adapted for mounting to the interface structure 18. The base 16 is typically planar, and comprises an aperture 44 for allowing the threaded portion of a first bolt 46 to be inserted therethrough, while enabling the bolt head to be seated on the shoulder 45. The base 16 further comprises a first alignment key 41 for aligning the base 16, and thus the prosthesis body 15 with the interface structure 18. As illustrated in FIGS. 3(*a*) and 3(*b*), the first alignment key 41 may be in the form of a projection, such as for example a radial tab, a plurality of longitudinally projecting pins, respectively, or indeed may be in any other suitable form (for example as described below for the second alignment key, mutatis mutandis), to engage with complementarily-shaped depressions, recesses or moldings 47 in the interface structure 18 to ensure proper alignment between the prosthesis body 15 and the interface structure 18. The base 16 is preferably rigid, though in variations of this embodiment it may be semi-rigid or non rigid, as will be described further herein. The prosthesis body 15 further comprises a bore 42 extending the longitudinal length of thereof, and of diameter greater than aperture 44, such as to expose occlusal-facing shoulder 45 of the base 16. The bore may be parallel sided, or tapering in either longitudinal direction, and may be circular, oval, polygonal or any other suitable shape in transverse cross-section. A plug 49, of suitable shape, typically complementarily to that of the bore 42 and dimensionally such as to provide a close fit or an interference fit, is provided for closing off the bore 42, after bolt 46 is inserted thereto and engaged with bore 55, as will become clearer hereinbelow.

The prosthesis body is typically non-reusable, and may be thrown away when the permanent prosthesis is eventually mounted on the implant. Optionally, though, the prosthesis body 15 may be made from a re-sterilisable or autoclavable material for multiple use.

The interface structure 18 is adapted for connecting the prosthesis body 15 to the implant 100, and comprises a partially internally threaded bore 55, complementarily threaded with respect to the bolt 46, and further comprises at an end thereof facing the implant 100 a second alignment key 51 that is adapted for seating with respect to a complementary recess, depression or molding 59 on the implant 100. Alignment key 51 is typically one of a variety of configurations designed to fit one of a variety of moldings 59 that may be found in the implant 100, for example according to the specific manufacturer thereof. Referring to FIGS. 4(*a*) and 4(*b*), typical second alignment keys may be in the form of a projecting right hexagon or square, or, as illustrated in FIG. 4(*c*), may be in the form of a projecting symmetrical star or polygon, allowing as many alternative alignment positions between the interface structure 18 and the implant 100 as there are planes of symmetry in the alignment key. Alternatively, the alignment key 51 may be in the form of a suitably shaped recess, while the moldings are projecting in an occlusal direction away from the implant 100. A shoulder 54 is provided at one end of the bore 55 for seating the head of second bolt 53, and a lower aperture 58 for allowing the threaded part of the bolt 53 to be inserted therethrough. The threaded part of the bolt 53 is complementarily threaded to the internally threaded bore 101 of the implant 100, and in use is engaged therewith.

The interface structure 18 includes a healing band 12 at the periphery thereof that promotes healing of the gum tissues, as will be further discussed hereinbelow. The interface structure 18 is typically made from a rigid material, but may also be made from less rigid materials. Thus, the interface structure 18 may be made from a metal, including for example any one of or combination of titanium, gold, or suitable alloys, ivory, porcelain, ceramics, plastics, Teflon, or any other biologically compatible materials, for example. The interface structure 18 is preferably reusable, and is thus made from a re-sterilisable or autoclavable material. Thus, given a particular implant 100, it is possible to choose an appropriate interface structure 18 from a selection thereof, such that has the appropriate structure for the specific second alignment key 51, for example, and to then choose an appropriate prosthesis body 15 to best match the missing tooth. This enables the dental practitioner to stock a kit comprising only a limited number of interface structures 18 according to the different types of implants 100 that he/she uses, and in which each interface structure 18 can be used, on the other hand, with all the prosthesis bodies in stock. This is possible, as all the interface structures 18 are configured for the same type of first alignment key 41 that is compatible with all the prosthesis bodies in stock. This set up avoids otherwise having to keep a plurality of full sets of temporary prostheses, in which each set is adapted for mounting to a particular type of implant.

As illustrated in FIGS. 5(*a*) and 5(*b*), the prosthesis body 15 may optionally be hollow, comprising an air-filled internal volume 50, enclosed between an outer resilient prosthesis skin 52 and an internal diaphragm or base 61. A suitable arrangement, for example a plug or skirt 62 is provided at a lower part of the skin 52, to engage with the base 16, preferably in a press-fit and aligned manner with respect thereto after the base 16 is properly secured to the interface structure 18 by means of bolt 46. Further, the skin 52 may comprise one or a plurality of apertures 63 that allow fluid communication between the volume 50 and the outside environment, enabling air inside the volume 50 to exit as the skin is inwardly deformed in response to the application of force or load F (FIG. 3(*a*)). When the load F is removed or reduced, the resilience of the skin 52 tends to return the same to its original shape, sucking air back into the volume 50. Optionally, and as may be the case for any variation of this embodiment, the base 16 may comprise a supplementary healing band 56 extending towards the skin and overlapping the same close to the base 16, for further assisting in the healing process of the gum tissues.

In a variation of the structure illustrated in FIGS. 5(*a*) and 5(*b*), the internal volume 50 is air tight and impermeable, i.e., without said apertures 63, and may be filled with a gel or liquid. Loads applied to the skin 52 enable the same to deform as the gel or liquid within the same redistributes therein. When the load is removed, the natural resilience of the skin returns this to its original shape, with the corresponding redistribution of gel or liquid. Optionally, the volume 50 may also include a volume of gas.

Further optionally, the prosthesis body 15 may comprise a structure that is per se load absorbing and which deforms to absorb loads or to prevents transmission of the loads, and returns to its original condition when the load is removed. For example, referring to FIG. 6, a plurality of metallic wires or strands in the form of a mesh, fabric or net form a resilient skeletal structure 55 in the form of the missing tooth. This skeletal structure 55 is fixed onto the base 16, which comprises aperture 44, and the skeletal structure 55 preferably comprises a suitable opening 61, typically at an upper end thereof occlusally displaced with respect to the base, for enabling the bolt 46 to be inserted thereto to engage the prosthesis body to the interface structure. The base 16 is typically also metallic, and the skeletal structure 55 may be overlaid with a sheath-like elastic skin 57 after the metallic structure of the prosthesis body is suitably secured to the interface structure 18. The skin 57 may be thin and while strong in terms of tearing or breaking, cannot in itself support a particular convex shape. Thus, without the skeletal structure 55, the skin 57 may substantially collapse under its own weight. However, when stretched over the skeletal structure 55, the latter provides the shape of the prosthesis body 15, while the skin 57 provides the outer color and appearance of the prosthesis 10. This arrangement for the prosthesis body 15 enables the same to be reused many times, discarding the skin 57 whenever the prosthesis 10 is used with a new patient (or when the skin is damaged with a particular patient, form example), while the skeletal structure 55 may be autoclaved or otherwise sterilized. Optionally, the strands retain a suitable amount of deformation when being molded to the desired prosthesis body shape by a suitable mold when subjected to a particular heat treatment. Materials for the strands may include, for example cobalt-based alloys, such as the low thermal expansion alloy "Elgiloy", or nickel based high strength alloys, such as for example "Hastelloy", nickel based heat treatable alloys, such as for example Incoloy, and some grades of stainless steel. In particular, the skeletal structure may be made from a shape-memory alloy, for example, which have a temperature induced phase change which causes the material to have a preferred configuration which can be fixed by heating the material to above a threshold temperature to induce a change in the phase of the material. When cooled down, the material will assume and return to the shape it was in during the treatment, unless constrained from doing so. Suitable examples of such a material may include Nickel Titanium alloys, for example "nitinol". The use of shape memory NiTi alloys in guidewires is known in the art, for example. Such NiTi alloys are commercially available and are also very elastic. A forming method for the skeletal structure 55 may thus comprise the steps of providing a mesh or the like comprising a plurality of strands formed of a metal which can be heat treated to substantially set a desired shape; deforming the mesh to generally conform to a surface of a molding element in the general shape of a desired dental prosthesis; heat treating the mesh in contact with the surface of the molding element to substantially set the shape of the mesh in its deformed state; and removing the mesh from contact with the molding element. The resulting mesh will define the skeletal structure which can stand external forces thereon, and revert to its original shape when the forces are removed, without substantially transmitting loads to the implant 100. Suitable materials for the skin 57 may include, for example, rubber, silicone, plastic, nylon, and so on.

Further optionally, and as illustrated in FIG. 7, particularly when the prosthesis body 15 is a solid, deformable body, the prosthesis body 15 may comprise a preformed weakened structure 69 that allows the prosthesis to deflect about said weakened structure 69 in response to application on the prosthesis of an externally-applied load F. The weakened structure 69 may comprise, for example, a zone in the body 15 that is significantly more flexible than the other parts of the body, comprising a weaker material, cavity, crack and so on thereat, or alternatively may comprise a film hinge or integral hinge, or the like.

As described above and illustrated in FIGS. 1 to 7, the prosthesis body may be designed to fully replace, albeit temporarily, the missing tooth. However, and further optionally, the prosthesis body may only represent a part of the tooth to be replaced, in particular the part that is most visible from outside the intraoral cavity during normal activities such as eating, smiling, talking, laughing and so on. Accordingly, and as illustrated in FIG. 8, the prosthesis may comprise a partial prosthesis body 85, having a base 46 that is configured for engagement with a corresponding interface structure (not shown). The partial prosthesis body 86 comprises an outwardly-facing surface 83, which is readily visible from outside the intraoral cavity, and an inwardly-facing wall 84 that is not easily or readily seen from that viewpoint. The partial prosthetic body 85 may thus be cantilevered with respect to a substantially larger base, and may be easily deflectable with respect thereto, absorbing loads rather than transmitting the same to the base.

A variation of the first embodiment is illustrated in FIG. 9, in which the temporary prosthesis 20 comprises a prosthesis body 25 and interface structure 28, similar to the prosthesis body 15 and interface structure 18 as described above, with the following differences, mutatis mutandis. Rather than the base 16 and bore 22, in this variation of the first embodiment the prosthesis body 25 has a non-rigid base 26 for abutting against the complementary facing surface 23 of the interface structure 28, and further comprises bore 27 extending through the length of body 25. The bore 27 has an outwardly stepped portion 24 comprising a shoulder 31 and well 32, comprised on the cusp portion of the prosthesis, opposed to the end thereof comprising base 26. The interface structure 28 may optionally comprise a pin 21 for mounting onto an implant 100 in an aligned manner therewith, and healing band 22, similar to the first embodiment, and the interface structure 28 comprises a threaded well 29. A suitable bolt 34, optionally comprising an enlarged head 35 and/or washer 36 is inserted in the bore 27 and threadingly engaged with the threaded well 29, such that the head 35 and/or washer 36 apply an abutting force between the body 25 and interface structure 28 via the shoulder 31. Once the body 25 is securely mounted to the interface structure 28, a suitably-shaped plug 37 may be inserted and optionally cemented or otherwise secured in well 32 to plug the same.

Figure 10:
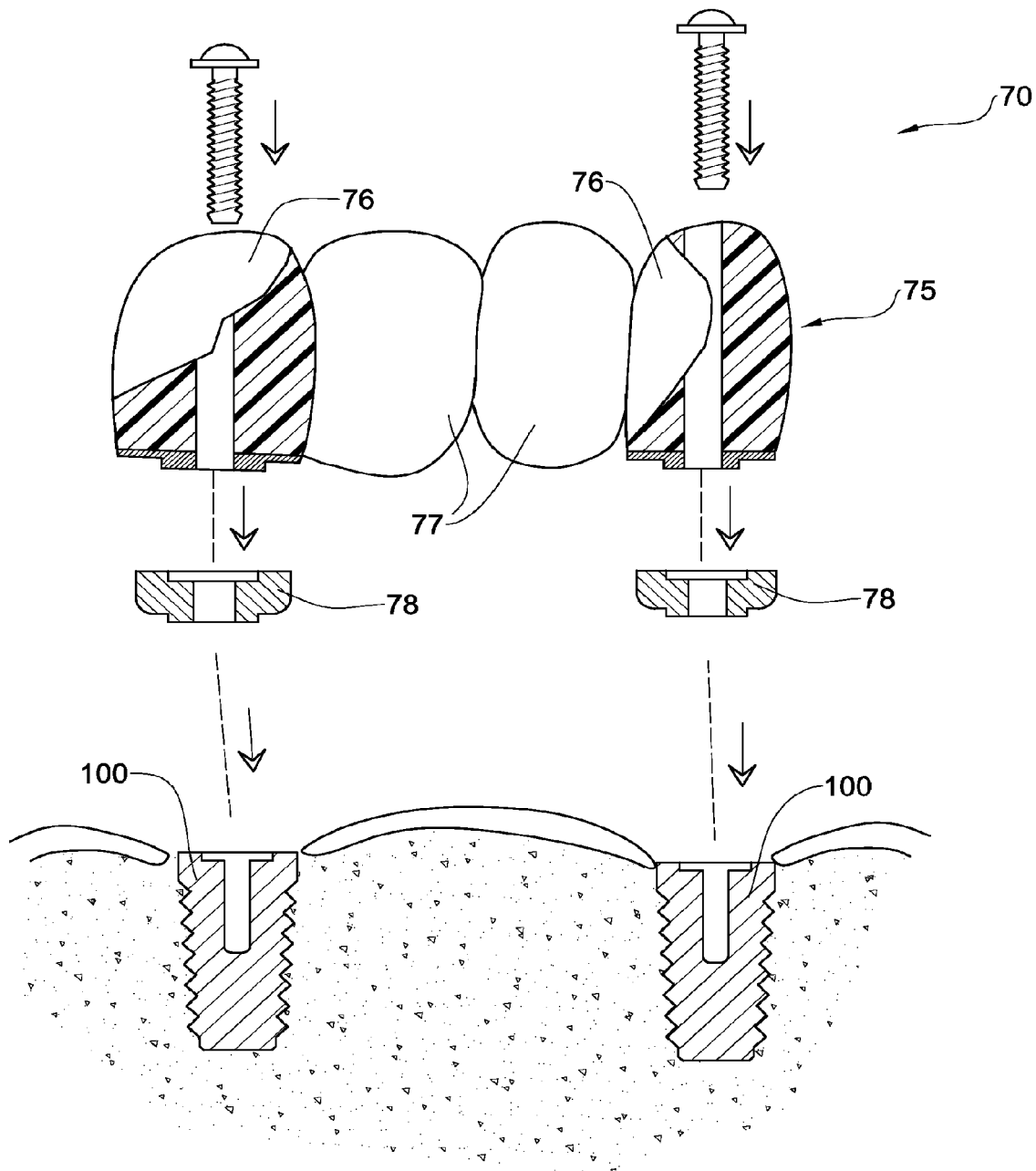
FIG. 10 illustrates another variation of the embodiment of FIG. 1, in the form of a bridge prosthesis.

Another variation of the first embodiment, particularly directed to bridge prostheses, is illustrated in FIG. 10, in which the temporary bridge prosthesis 70 comprises a composite prosthesis body 75 and a pair of interface structures 78. In this embodiment, the composite prosthesis body 75 comprises a temporary pontic 77 designed to fit in the edentulous space, and joined at each lateral end thereof to one of two retainer bodies 76. Each retainer body 76 and interface structure 78 may be similar to the prosthesis body 15 and interface structure 18 as described above, mutatis mutandis. In particular, though, the retainer bodies 76 are configured for being joined with the pontic 77, either integrally, by bonding, mechanical connection, reversibly or in any other manner. The pontic itself may also comprise a similar construction to that of the retainer bodies 76, being flexible and absorbing forces by deforming rather than transmitting loads to the implants 100, though typically the pontic 77 does not require structural elements for connection to an interface structure. Each retainer body 76 preferably comprises a bore 73 enabling a through bolt 72 to reach and engage the corresponding implant 100, via interface structure 78, which may comprise simple bores to accommodate the bolts with a clearance. In this embodiment, the interface structures 78 are each properly secured to the corresponding implants 100 in proper alignment therewith and with respect to the retainer bodies 76, the implants 100 being already embedded in the bony tissues, so that the prosthesis body 75 may be secured to the interface structures 78 via the corresponding interface structures 78.

Figure 11A:
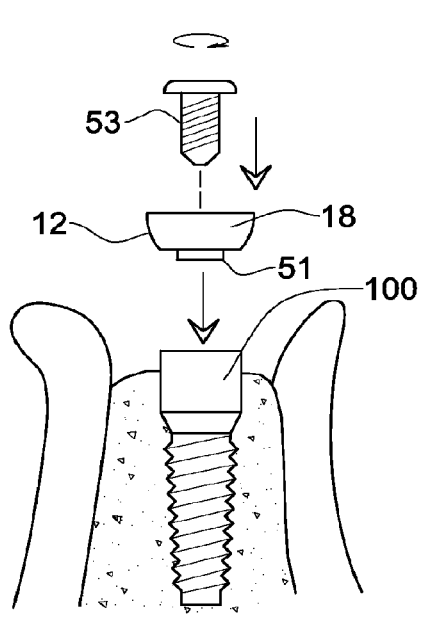
FIGS. 11(a) to 11(d) illustrate a procedure for installing a crown prosthesis, in which a temporary prosthesis according to the embodiment of FIG. 1 is used in an intermediate stage.
Figure 11B:
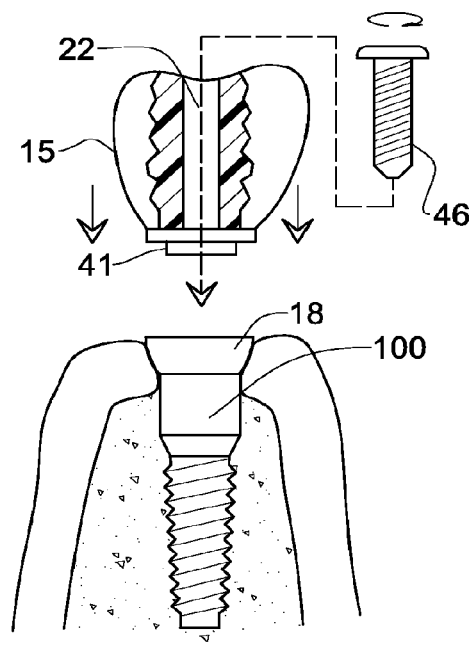
Figure 11C:
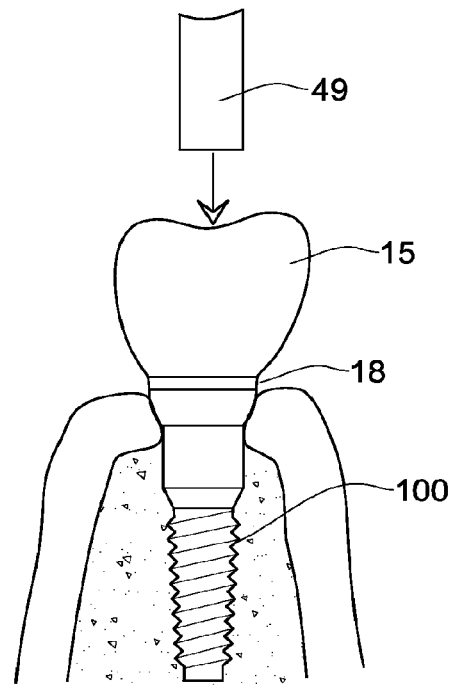
Figure 11D:
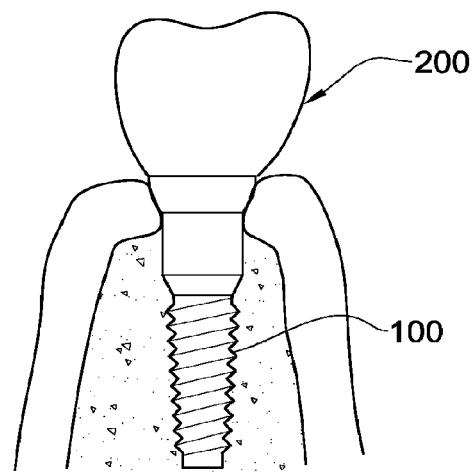

The temporary prosthesis according to the first embodiment may be used in a general procedure for mounting a permanent implant as follows. While the procedure is being illustrated with respect to a crown prosthesis, of the particular type illustrated in FIG. 1, the procedure for other types of crown prostheses and for bridge prostheses is similar thereto, mutatis mutandis. Referring to FIG. 11(a), in the surgical phase a suitable implant 100, is first screwed or tapped into a surgically prepared site in the upper or lower jaw 99, and this procedure is well known in the art. Then, a suitable interface structure 18 having an appropriate second alignment key 51 that is compatible with the implant 100, is locked in place with respect to the implant by means of bolt 53, such that the healing band 12 is abutting the open gum line. Referring to FIG. 11 (b), the temporary prosthesis body 15 is then mounted to the interface structure 18, aligned therewith via the first alignment key 41, and secured therein via bolt 46, after which the plug 49 is inserted in the bore 22 to close off the same (FIG. 1(c)). The temporary prosthesis 10 remains in place, typically for 3 to 6 months, until the osseointegration process is completed, and the implant is firmly anchored in the jaw. Should the prosthesis body 15 and/or the interface structure 18 be damaged, it may be replaced relatively easily. Similarly, if there is evidence of infection, the temporary prosthesis 10 may be removed temporarily, and the infection treated. During this time, the patient has the advantage of having a prosthesis with the likeness and form of the missing tooth, while at the same time the gum is healed, and substantially no loads are transmitted to the implant, avoiding micromovements thereof as the loads on the prosthesis body are absorbed rather than transmitted. At the end of the osseointegration process, the temporary prosthesis 10 is removed, and a permanent prosthesis 200 is mounted to the implant 100, FIG. 11(d). Optionally, the permanent prosthesis 200 may comprise a single integral unit, as illustrated, or may comprise a cap portion, and an interface structure for connecting the cap portion to the implant.

Another variation of the first embodiment is illustrated in FIG. 12, and comprises all the elements and features as described herein with respect thereto, with the following differences, mutatis mutandis. The base 16' comprises in this embodiment a threaded well 17' that extends in the occlusal direction C away from the direction of the implant 100 rather than the bore 42 and plug 49 illustrated in FIG. 1. Further, the interface structure comprises a first pin 19' comprising external threads complementary to the internal threaded structure of the well 17', and an opposed second pin 11' suitably threaded or otherwise configured to be received and reversibly locked in the implant 100. Of course, instead of the threaded structure for the first or second pins, these may comprise any suitable engagement configuration, for example a snap-fit or bayonet-fit arrangement. The second pin 11' may thus comprise any one of a plurality of suitable configurations that enable the interface structure 18' to be mounted onto one of a variety of different types of implants 100, made by different manufacturers for example. Alternatively, instead of engaging pin 19' to well 17', the body 15' and interface structure 18' may comprise complementary faces via which the two components may be cemented, bonded or welded together, permanently or reversibly.

In particular, the prosthesis body 15' and interface structure 18' for this variation of the first embodiment of the prosthesis 10' are engineered such that when the interface structure is fully engaged in the implant 100, and when the prosthesis body is fully engaged with the interface structure, the prosthesis body, interface structure and implant are aligned in a particular manner. Suitable indicia or markings 67 in these components may be provided for guiding the user, and the markings give a measure of the departure from alignment according to the mismatch between complementary markings in each pair of adjacent components. In particular, the marking in the implant itself may be provided at a position that guides the user when installing the implant such that the implant should be in a particular orientation with respect to this marking. For example, the marking could be set to be placed in the mesio-distal direction facing the interproximal zone with respect to the adjacent tooth. Once the implant is properly fixed in relation to the intraoral cavity, the interface structure and the prosthesis body will be automatically aligned therewith by aligning the markings therein.

Another variation of the embodiment of FIG. 12 is illustrated in FIG. 13, in which the temporary prosthesis 60 comprises a prosthesis body 65 and interface structure 68, similar to the prosthesis body 15' and interface structure 18' as described above, with the following differences, mutatis mutandis. Rather than the threaded well 17', in this variation of the first embodiment the prosthesis body 65 has a threaded pin 69 extending in the direction of the interface structure 68, and designed to engage in a threaded well 67 comprised therein. The body 65 is securely mounted to the interface structure 68 by screwing the pin 69 into the threaded bore 67.

Figure 14A:
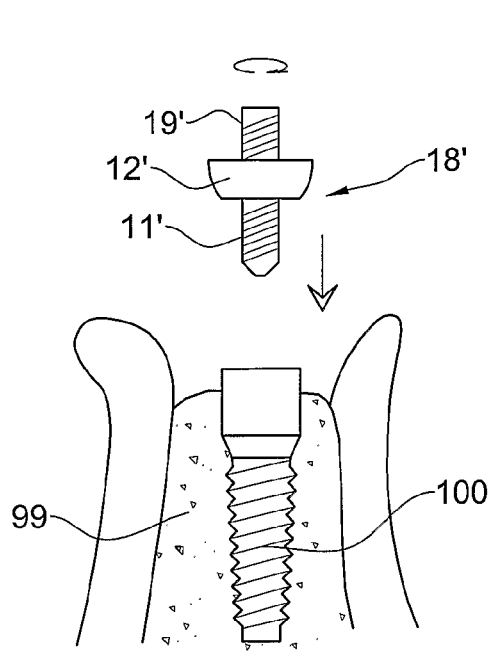
FIGS. 14(a) to 14(d) illustrate a procedure for installing a crown prosthesis, in which a temporary prosthesis according to the embodiment of FIG. 12 is used in an intermediate stage.
Figure 14B:
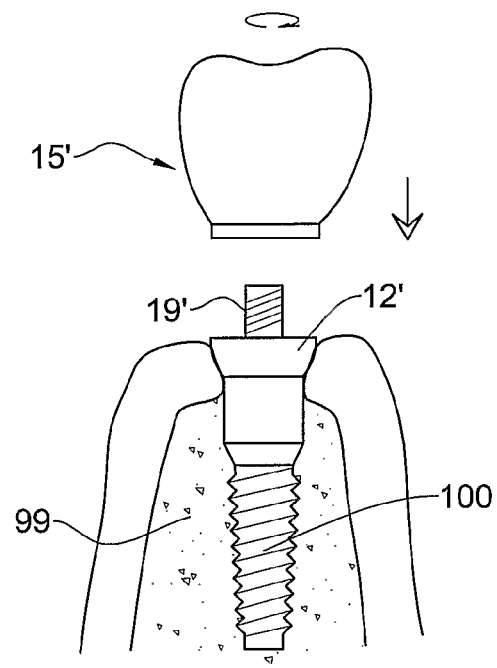
Figure 14C:
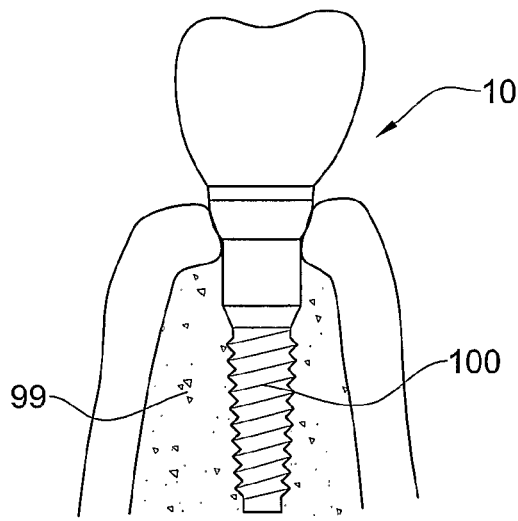
Figure 14D:
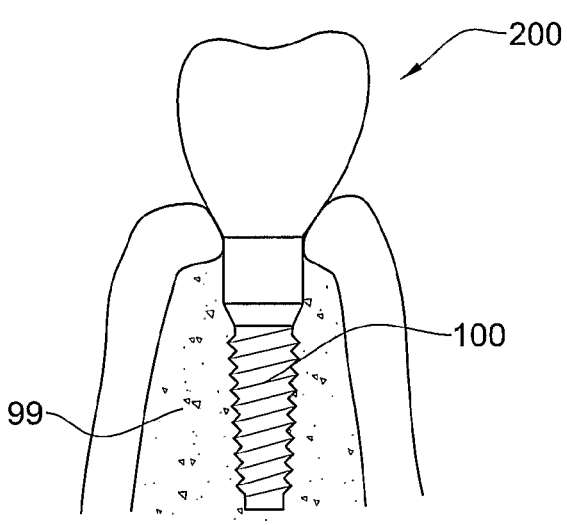

The temporary prosthesis according to the embodiment of FIG. 12 may be used in a general procedure for mounting a permanent implant in a similar manner to that described above in connection with FIGS. 11(a) to 11(d), with some differences as follows, mutatis mutandis. Thus, referring to FIG. 14(a), in the surgical phase a suitable implant 100, is first screwed or tapped into a surgically prepared site in the upper or lower jaw 99, such that the implant is properly aligned in the jaw. In FIG. 14(b), a suitable interface structure 18' having an appropriate second pin 11' that is compatible with the implant 100, is locked in place with respect to the implant in alignment therewith, and such that the healing band 12' is abutting the open gum line. The temporary prosthesis body 15' is then mounted to the interface structure 18' in proper alignment therewith, FIG. 11(c), and remains there until the osseointegration process is completed, and the implant is firmly anchored in the jaw, after which the temporary prosthesis 10' is removed, and a permanent prosthesis 200 is mounted to the implant 100, FIG. 14(d). Optionally, the permanent prosthesis 200 may comprise a single integral unit, as illustrated, or may comprise a cap portion, and an interface structure for connecting the cap portion to the implant.

A temporary prosthesis according to a second embodiment of the present invention, illustrated in FIG. 15 and generally designated with the numeral 110, is generally similar to the first embodiment or any variation thereof, as described above, mutatis mutandis, with a main difference as follows. The temporary prosthesis 110 according to the second embodiment comprises a prosthesis body 125, and an integral interface structure 128 for connection to the implant 100 that in typical use is already surgically implanted in the bony tissues 99 of the patient. Thus, while the two components of the prosthesis—the body 125 and the interface structure 128— may be made, for example, from different materials and having different load absorbent properties, similar to the prosthesis body and interface structure respectively of the first embodiment, there is no reversibly interconnecting means between the two components, which are instead permanently joined together in use. Thus, as with first embodiment illustrated in FIG. 1, mutatis mutandis, the second embodiment of the prosthesis illustrated in FIG. 15 comprises a load absorbent body made from a resilient material, and is attached to a interface structure. The prosthesis body 125 comprises a stepped bore structure 127, similar to that described with respect to FIG. 9 in the first embodiment, mutatis mutandis. The interface structure here comprises base 126 that is adapted for abutment with the exposed face 123 of the implant 100, and a bolt 134 optionally including a washer 136 and/or an enlarged head 135, wherein the bolt threadingly engages the implant 100, securely holding the body 125 to the implant 100. A suitable alignment key 181, complementary to molding 182 on the implant 100, enables the prosthesis 125 to be properly aligned with the implant 100. Plug 137 covers the outer enlarged part of the bore 127. In this configuration, while the prosthesis body 125, from the head 135 to the base 126, cannot generally sway with respect to the implant 100, the body 125 can nevertheless absorb loads.

Figure 15:
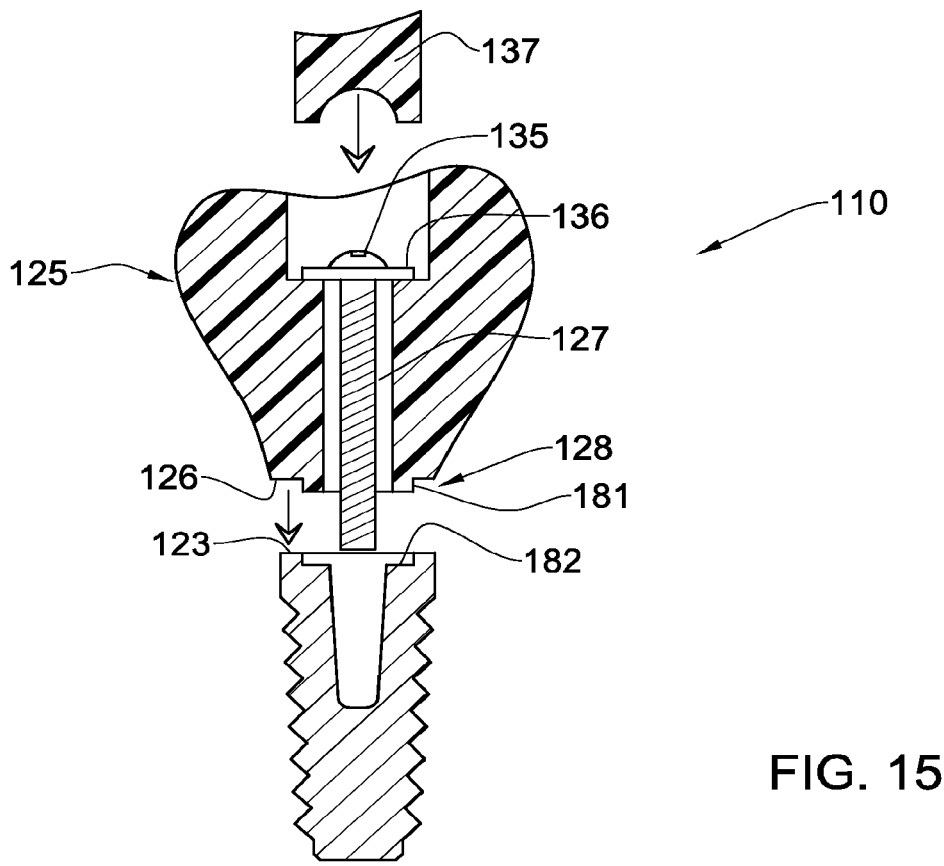
FIG. 15 illustrates in side cross-sectional view a second embodiment of the invention.
Figure 16:
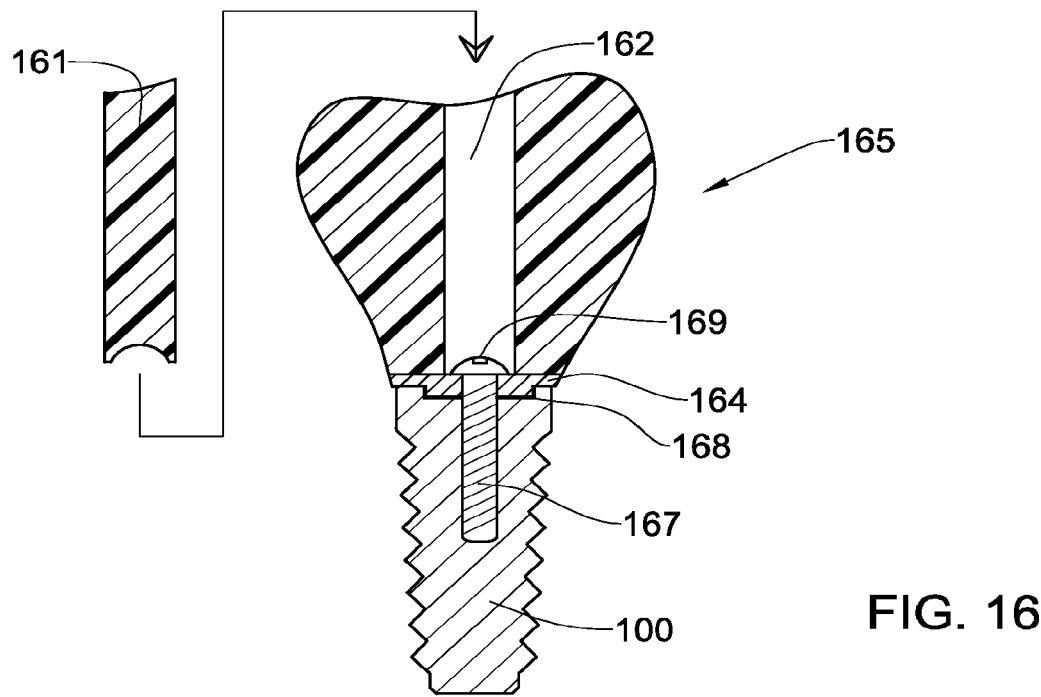
FIG. 16 illustrates a variation of the embodiment of FIG. 11.

Yet another variation of the second embodiment, illustrated in FIG. 16, is similar to that illustrated in FIG. 15, mutatis mutandis, with the following major differences. The prosthesis body 165 comprises an integral base 166, made preferably from a rigid or semi rigid material, and the bolt 167 secured the prosthesis body 165 by abutment of the head 169 and/or washer 164 against an exposed flange 168 comprised in the base 166. The bolt 167 is inserted in position via the bore 162, which can be plugged with elongate plug 161. In this configuration, practically the full prosthesis body 165, from the head 135 to the base 126, may sway or deform with respect to the implant 100, to absorb loads.

Figure 17:
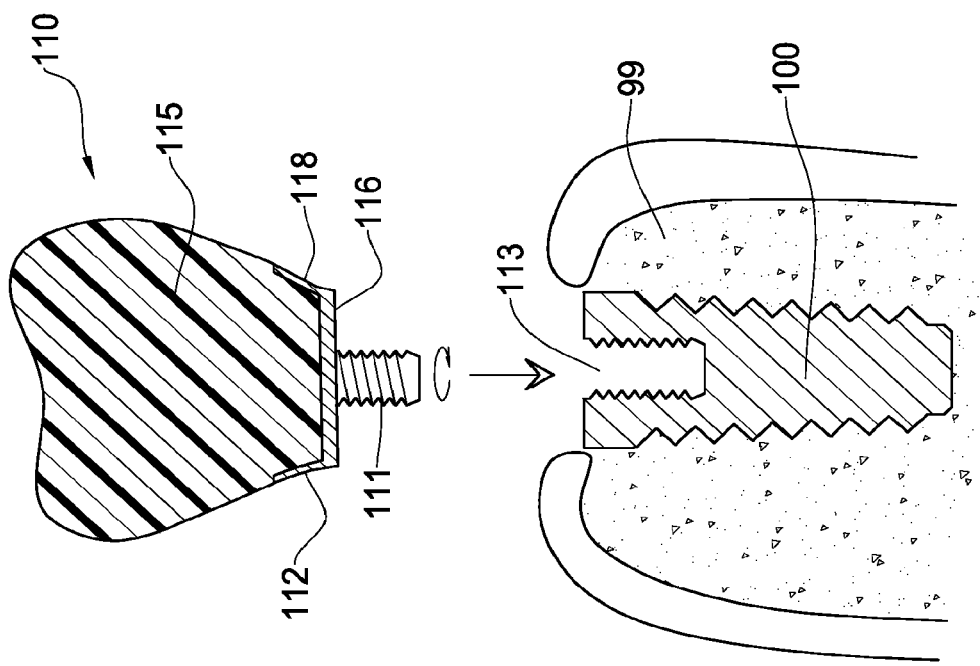
FIG. 17 illustrates another variation of the embodiment of FIG. 11.

A variation of the second embodiment is illustrated in FIG. 17, which is similar to the variation of the first embodiment illustrated in FIG. 12, comprises a base 116 and a pin 111 similar to pin 11' thereof, enabling the prosthesis 110 to be connected to an implant having the corresponding connection configuration 113. Preferably, a healing band 112 depends from the outer edge of the base 116 in a direction opposed to the pin 111.

Figure 18:
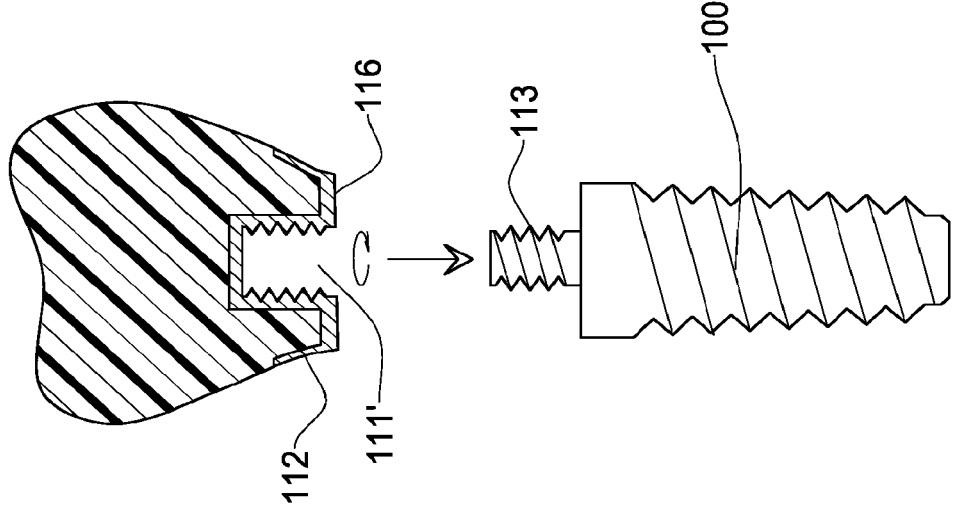
FIG. 18 illustrates another variation of the embodiment of FIG. 11.

Another variation of the second embodiment is illustrated in FIG. 18, wherein rather than a pin 111, the base 116 comprises a threaded well 111' for threadingly engaging the connection configuration 113' of the implant 100, which for this particular implant is in the form of a protruding threaded pin 113'.

In other variations of the second embodiment, the prosthesis body may be similar to that described herein for other variations of the first embodiment, for example as described above, mutatis mutandis.

The temporary prosthesis according to the second embodiment may be used in a general procedure for mounting a permanent implant in a similar manner to that described for the first embodiment with respect to FIGS. 11(a) to 11(d), or FIGS. 14(a) to 14(d), with the following major differences, mutatis mutandis. As with the first embodiment, the first stage is to install the implant 100 into the prepared site. Then, the full temporary prosthesis is connected to the implant as a unit, and properly aligned thereto, and preferably such that the healing band is in contact with the healing gum tissue. After the osseointegration process is completed, the temporary prosthesis is removed, and replaced with the permanent prosthesis. As with the first embodiment, where the prosthesis is for a bridge, the mounting procedure is concurrently executed at the two implants to secure the two retainer bodies, which of course include integral interface structures.

Optionally, the temporary prosthesis according to the first or second embodiments may be provided to a particular patient in any one of varying degrees of softness. For example while one patient may prefer to have a very soft prosthesis, perhaps due to very delicate gums, such that loads are almost totally absorbed by the prosthesis, other patients may prefer a less soft prosthesis, which may on the other hand be sturdier, and only deflect or deform when the loads acting on it exceed a predetermined threshold that would be detrimental to the osseointegration process, according to some predetermined criteria. Typically, the flexibility and load-absorbing properties of the temporary prosthesis is chosen so that it is suitable for the position of the jaw in which it is to be mounted, and according to the expected loads. Optionally, a particular patient may be provided with a set of temporary prostheses of varying softness for the same dental site, such that at the beginning of the osseointegration process the softest prosthesis is mounted to the implant, and the prosthesis is replaced with progressively less soft prosthesis as the implant gets more and more firmly planted in the jaw.

In the method claims that follow, alphanumeric characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed exemplary embodiments in accordance with the invention, it will be appreciated that many changes may be made therein without departing from the spirit of the invention.

The invention claimed is:

1. A temporary dental prosthesis comprising:
a prosthesis body and at least one interface structure configured for mounting said prosthesis to at least one implant, wherein:
said prosthesis body comprises an external surface having a shape resembling that of a respective tooth,
said prosthesis body is configured for substantially absorbing externally-applied loads acting on the prosthesis body and for minimizing transmission of such externally-applied loads to at least the implant onto which said temporary prosthesis is to be mounted,
said shape of said prosthesis body external surface is deformed responsive to application of the externally-applied loads on said prosthesis body, and
said prosthesis body external surface is more resilient than the at least one interface structure.

2. The prosthesis according to claim 1, wherein said prosthesis body is made from a load-absorbing material.

3. The prosthesis according to claim 2, wherein said load-absorbing material comprises a resilient material capable of absorbing said loads by substantially being deformed from a nominal datum shape.

4. The prosthesis according to claim 2, wherein said prosthesis body comprises at least one pre-formed weakened structure configured to enable a first part of said prosthesis to deflect about said at least one pre-formed weakened structure in response to application thereon of said externally-applied loads.

5. The prosthesis according to claim 4, wherein
said at least one pre-formed weakened structure is configured to enable said first part of said prosthesis to break off from said prosthesis body in response to application thereon of said externally-applied loads having a magnitude greater than a predetermined threshold, wherein
said threshold is correlated to a predetermined safety limit configured to prevent excessive loads being transmitted to said implant onto which the prosthesis body is to be mounted.

6. The prosthesis according to claim 2, wherein said load-absorbing material comprises a material selected from the group consisting of: rubber, silicone, nylon, polyethylene, copolymers, plastic, Teflon, compomers, elastomers, and other biocompatible materials.

7. The prosthesis according to claim 3, wherein said prosthesis body is substantially a solid body made of said resilient material.

8. The prosthesis according to claim 2, wherein said prosthesis body is made from a plurality of layers of suitable materials.

9. The prosthesis according to claim 2, wherein
said prosthesis body is deformed under said externally-applied loads such that at least one part of the external surface of the prosthesis body is displaced from an unstressed datum position by a displacement, wherein
under said externally-applied loads corresponding to regular masticating actions between the jaws, said displacement is in the range of about 0.5 mm to about 5 mm.

10. The prosthesis according to claim 1, wherein said prosthesis body comprises a load-absorbing structure capable of absorbing said externally-applied loads by substantially being deformed from a nominal datum shape.

11. The prosthesis according to claim 2, wherein said at least one interface structure comprises an engagement arrangement for engaging the prosthesis with said implant.

12. The prosthesis according to claim 11, wherein said at least one interface structure comprises a healing band at a periphery thereof adapted for promoting healing of gum tissues when said at least one interface structure is connected to said implant.

13. The prosthesis according to claim 11, wherein said at least one interface structure comprises at least one material selected from the group consisting of: titanium, gold, metal alloys, ivory, porcelain, ceramics, plastics, Teflon, and any other biologically compatible material.

14. The prosthesis according to claim 2, wherein said prosthesis body is a crown prosthesis.

15. The prosthesis according to claim 2, wherein
said prosthesis is a bridge prosthesis and comprises at least two spaced interface structures, each adapted for mounting onto separate implants, and
further comprises a pontic section connected laterally on either side thereof to one of two retainer portions, wherein
each of said retainer portions comprises one of said spaced interface structures.

16. The prosthesis according to claim 1, wherein said prosthesis body is integrally joined to said interface structure.

17. A kit of temporary prostheses, comprising
a plurality of different prosthesis bodies and a plurality of interface structures as defined in claim 1, and
further comprising a mounting arrangement for mounting said prosthesis to one of said interface structures, wherein
each of said interface structures is adapted for mounting to one of a variety of said implants, and
wherein each of said interface structures is adapted for mounting to one of said plurality of prosthesis bodies.

18. A method for implanting a permanent prosthesis onto at least one implant embedded in an intraoral cavity, comprising:

(a) embedding one of said at least one implant such that an upper part thereof is exposed with respect to surrounding gingiva;
(b) during a healing period of the one of said at least one implant with respect to bone tissue associated with said embedding step (a), mounting a temporary prosthesis on the one of said at least one implant, wherein:
said temporary prosthesis comprises an external surface having a shape resembling that of a respective tooth,
said prosthesis body is configured for substantially absorbing externally-applied loads acting thereon and for minimizing transmission of such externally-applied loads to the one of said at least one implant,
said shape of said prosthesis body external surface is deformed responsive to application of the externally-applied loads on said prosthesis body, and
said prosthesis body external surface is more resilient than the at least one interface structure; and
(c) after said healing period replacing said temporary prosthesis with a substantially non-deformable permanent prosthesis capable of reacting to and transmitting the externally-applied loads to the one of said at least one implant.

19. The method according to claim 18, wherein
said prosthesis body is integrally joined to the one of said at least one interface structure.

20. The method according to claim 18, wherein
said prosthesis body is reversibly mountable with respect to the one of said at least one interface structure.

21. The prosthesis according to claim 2, wherein said prosthesis body is a bridge prosthesis, and comprises at least two spaced interface structures, each adapted for mounting onto separate implants.

22. The prosthesis according to claim 1, wherein said prosthesis body is reversibly mountable with respect to one of said at least one interface structure.

23. The prosthesis according to claim 3, wherein
said prosthesis body comprises a cavity and a skin enclosing said cavity made of said resilient material, said skin defining said external surface.

24. A temporary dental prosthesis comprising:
a prosthesis body and at least one interface structure configured for mounting said prosthesis to at least one implant, wherein:
said prosthesis body comprises an external surface having a shape resembling that of a respective tooth,
said prosthesis body external surface is configured for substantially absorbing externally-applied loads acting on the prosthesis body and for minimizing transmission of such externally-applied loads to at least the implant onto which said temporary prosthesis is to be mounted,
said prosthesis body external surface is more resilient than the at least one interface structure, and
said interface structure is made from a rigid or semi rigid material.

* * * * *